(12) United States Patent
Beumer

(10) Patent No.: US 9,296,677 B2
(45) Date of Patent: Mar. 29, 2016

(54) SYNTHESIS OF PERETINOIN

(75) Inventor: Raphael Beumer, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/877,241

(22) PCT Filed: Sep. 29, 2011

(86) PCT No.: PCT/EP2011/066964
§ 371 (c)(1),
(2), (4) Date: Jul. 8, 2013

(87) PCT Pub. No.: WO2012/041949
PCT Pub. Date: Apr. 5, 2012

(65) Prior Publication Data
US 2013/0281736 A1    Oct. 24, 2013

(30) Foreign Application Priority Data
Oct. 1, 2010 (EP) .................................. 10185739

(51) Int. Cl.
*C07C 51/377* (2006.01)
*C07C 51/353* (2006.01)
*C07C 67/343* (2006.01)
*C07F 9/11* (2006.01)
*C07F 9/40* (2006.01)
*C07F 9/50* (2006.01)
*C07F 9/54* (2006.01)

(52) U.S. Cl.
CPC ............. *C07C 51/377* (2013.01); *C07C 51/353* (2013.01); *C07C 67/343* (2013.01); *C07F 9/11* (2013.01); *C07F 9/4015* (2013.01); *C07F 9/5004* (2013.01); *C07F 9/5022* (2013.01); *C07F 9/5428* (2013.01); *C07F 9/5442* (2013.01)

(58) Field of Classification Search
CPC ..... C07C 51/353; C07C 67/343; C07C 57/03; C07C 69/587; C07C 51/377; C07F 9/11; C07F 9/4015; C07F 9/5004; C07F 9/5022; C07F 9/5428; C07F 9/5442
USPC ........................................................ 562/598
See application file for complete search history.

(56) References Cited

U.S. PATENT DOCUMENTS

| 6,423,873 | B1 * | 7/2002 | Wegner et al. ..................... 568/9 |
| 7,015,353 | B2 * | 3/2006 | Soukup et al. ................. 562/510 |
| 2002/0198411 | A1 * | 12/2002 | Tanikawa et al. ............. 568/391 |
| 2007/0004925 | A1 * | 1/2007 | Ernst et al. ..................... 549/369 |

FOREIGN PATENT DOCUMENTS

| CN | 1319600 | 10/2001 |
| CN | 1771227 | 5/2006 |
| CN | 101035748 | 9/2007 |

OTHER PUBLICATIONS

International Search Report for PCT/EP2011/066964 mailed Dec. 15, 2011.
J.B. Davis et al., "Carotenoids and Related Compounds. Part XV. The Structure and Synthesis of Phytoene, Phytofluene,. Zeta.-Carotene, and Neurosporene", Journal of the Chemical Society, Section C: Organic Chemistry, Chemical Society, Jan. 1, 1966, pp. 2154-2165.
Ono et al; "*Reaction of α-(Phenylsulfinyl)acetonitrile with Aldehydes and Ketones to γ-Hydroxyalkenenitriles and Syntheses of Terpenoids*", J.Am.Chem.Soc. 1984, 106, 7890-7893.
CN Appln. No. 201180047762.1, The Second Office Action, Jan. 4, 2015.

* cited by examiner

*Primary Examiner* — Jafar Parsa
*Assistant Examiner* — Amy C Bonaparte
(74) *Attorney, Agent, or Firm* — Nixon & Vanderhye P.C.

(57) ABSTRACT

The present invention relates to a new and improved synthesis of peretinoin.

1 Claim, No Drawings

SYNTHESIS OF PERETINOIN

This application is the U.S. national phase of International Application No. PCT/EP2011/066964 filed 29 Sep. 2011 which designated the U.S. and claims priority to EP 10185739.9 filed 1 Oct. 2010, the entire contents of each of which are hereby incorporated by reference.

The present invention relates to a new and improved synthesis of peretinoin.

Peretinoin (also known as NIK 333) is an acyclic retinoid. This compound is us useful in reducing the recurrence of hepatocellular carcinoma (HCC) after surgical resection or ablation in hepatitis C virus (HCV) positive patients.

Liver cancer is the sixth most common cancer in the world, and more than six hundred thousand patients are newly diagnosed every year. In Japan, liver cancer is the third leading cause of death from cancer. The newly diagnosed patients are about 40,000, and about 35,000 patients die every year. Primary liver cancer is classified into HCC and cholangiocellular carcinoma, and about 94% is HCC. HCC are mainly caused by the infections of hepatitis B virus or HCV, and in Japan about 67% of HCC are caused by the HCV. HCV positive HCC is known to have a high recurrence rate after curative resection, and the recurrence rates are 24%, 76%, 92% within 1, 3, 5 years, respectively.

Peretinoin is an important compound in the fight against liver cancer. Therefore any improved way to synthesise is important.

The present invention relates to an improved process of production of peretinoin, wherein the process can be carried as a one-pot-reaction. A further advantage of the new process is that the amount salts (used as well as formed during the various steps) is low, which results in less waste products. Furthermore this process can be carried out as a one-pot reaction, which results in an easier handling (no isolation of intermediates).

Therefore the process of production of peretinoin is characterised in that it comprises the following reaction (step a):
(a) the compound of formula (I) or formula (I'),

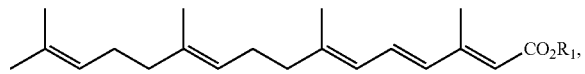

(I)

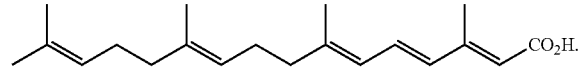

(I')

wherein
$R_2$ is substituted phenyl, unsubstituted phenyl, —$(CH_2)_3$—OH, or —$(CH_2)_3$—$CH_3$,
$R'_2$ is $OC_1$-$C_4$alkyl, and
X is a halogen ion, preferably I and Br,
is reacted with a compound of formula (II)

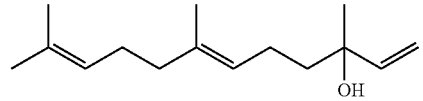

(II)

wherein $R_1$ is H or a $C_1$-$C_4$ alkyl group.

The obtained reaction product from this step is the compound of formula (III)

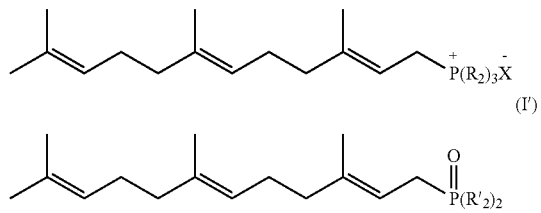

(III)

wherein $R_1$ is H or a $C_1$-$C_4$ alkyl group.
NIK 333 is the compound of formula (IIIa)

(IIIa)

To obtain a compound of formula (I) the following process of production can be carried out (step b):
a compound of formula (IV)

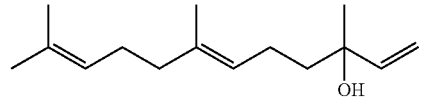

(IV)

is reacted with HX, wherein
X is a halogen atom, preferably, I or Br
and a compound of formula (V)

$P(R_2)_3$ (V), wherein $R_2$ is substituted phenyl, unsubstituted phenyl, —$(CH_2)_3$—OH, or —$(CH_2)_3$—$CH_3$. The reaction product thereof is a compound of formula (I) as described above.

To obtain a compound of formula (I') the following process of production can be carried out (step b'):
a compound of formula (IV)

(IV)

is reacted with HX, wherein
X is a halogen atom, preferably, I or Br
and a compound of formula (V')

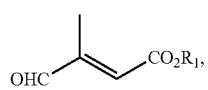

(V')

wherein $R'_2$ is $OC_1$-$C_4$alkyl. The reaction product thereof is a compound of formula (I') as described above.

As mentioned above the advantages of the process according to the present invention is that this process is part of a series of reactions steps, which can be carried out as a one-pot reaction and wherein the amount of salt (used as well formed during the reactions) is low. In the following the various reactions steps are discussed in more details.

Step a)

This reaction is usually carried out in an inert organic solvent or in a mixture of such solvents. Suitable solvents are i.e. alcohols, such as methanol, ethanol, n-butanol and i-propylalcohol; $CH_3CN$; $CH_2Cl_2$; THF; DMF; acetic acid ester; hexane; cyclohexane and toluol.

Usually a base (or a mixture thereof) is added to the reaction. Suitable bases are i.e. BuLi, NaOMe and NaOEt. The reaction is preferably carried out under atmospheric pressure. The reaction is preferably carried out at room temperature (20° C. to 25° C.) or at a temperature up to 60° C.

Step b) and b')

This reaction is usually (and preferably) carried out in the same inert organic solvent or in a mixture of such solvents as in step a). Suitable solvents are i.e. .e. alcohols, such as methanol, ethanol, n-butanol and i-propylalcohol; $CH_3CN$; $CH_2Cl_2$; THF; DMF; acetic acid ester; hexane; cyclohexane and toluol. Usually a base (or a mixture thereof) is added to the reaction. Suitable bases are i.e. BuLi, NaOMe and NaOEt.

The reaction is preferably carried out under atmospheric pressure. The reaction is preferably carried out at temperature from 0° C. to 80° C.

The reaction conditions for step b') are the same as for b).

The invention claimed is:

1. A process for the production of a peretinoin compound of formula (IIIa):

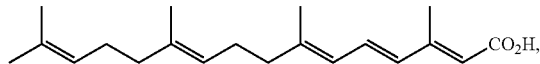

(IIIa)

wherein the process comprises the following steps:
(a) reacting a compound of formula (I) or (I'),

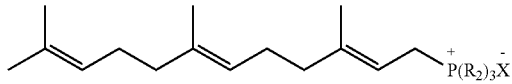

(I)

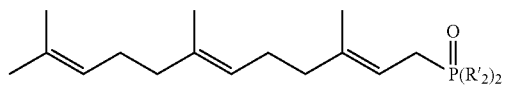

(I')

wherein
R$_2$ is substituted phenyl, unsubstituted phenyl, —(CH2)3-OH, or —(CH2)3-CH3,
R'$_2$ is OC$_1$-C$_4$ alkyl, and
X is a halogen ion,
with a compound of formula (II)

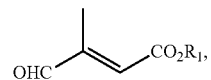

(II)

wherein R$_1$ is H, and
(b) forming the compound of formula (I) or formula (I') by reacting a compound of formula (IV):

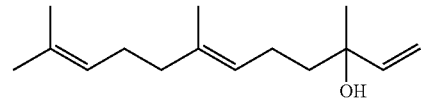

(IV)

with HX, wherein X is I or Br, and
a compound of formula (V) or formula (V')

$P(R_2)_3$, (V)

(V')

wherein
R$_2$ is phenyl, —(CH$_2$)$_3$—OH, or —(CH$_2$)$_3$—CH$_3$, and
R'$_2$ is OC$_1$-C$_4$ alkyl, wherein
the reactions of steps (a) and (b) are carried out in a one-pot-reaction in the presence of the same inert organic solvent.

* * * * *